(12) United States Patent
Brock et al.

(10) Patent No.: US 6,447,554 B1
(45) Date of Patent: Sep. 10, 2002

(54) REACTIVE DYE COMPOUNDS

(75) Inventors: Earl David Brock, West Chester, OH (US); David Malcolm Lewis, Otley; Taher Iqbal Yousaf, Egham, both of (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/647,584

(22) PCT Filed: Apr. 1, 1999

(86) PCT No.: PCT/US99/07291
§ 371 (c)(1),
(2), (4) Date: Oct. 2, 2000

(87) PCT Pub. No.: WO99/51689
PCT Pub. Date: Oct. 14, 1999

Related U.S. Application Data

(63) Continuation of application No. PCT/US98/06561, filed on Apr. 2, 1998.

(51) Int. Cl.[7] .................................................. A61K 7/13
(52) U.S. Cl. .................................. 8/549; 8/543; 8/428
(58) Field of Search ........................... 8/549, 543, 471, 8/428, 642, 685, 918; 540/126; 544/180, 224, 242; 534/634, 637, 638

(56) References Cited

U.S. PATENT DOCUMENTS

| | | | | |
|---|---|---|---|---|
| 5,735,911 A | * | 4/1998 | Tzikas | 8/547 |
| 5,760,193 A | * | 6/1998 | Russ et al. | 534/605 |
| 5,780,602 A | * | 7/1998 | Schumacher et al. | 534/642 |
| 5,785,745 A | * | 7/1998 | Lauw et al. | 106/31.27 |
| 5,914,444 A | * | 6/1999 | Reinert et al. | 8/442 |
| 5,944,855 A | * | 8/1999 | Lehmann et al. | 8/549 |
| 5,958,086 A | * | 9/1999 | Adam et al. | 8/641 |
| 5,968,208 A | * | 10/1999 | Taylor | 8/543 |
| 5,976,197 A | * | 11/1999 | Hutchings et al. | 8/543 |
| 6,159,250 A | * | 12/2000 | Patsch | 8/549 |

FOREIGN PATENT DOCUMENTS

| | | | | |
|---|---|---|---|---|
| BE | 644 495 A | | 8/1964 | |
| CH | 540/62 A4 | | 6/1964 | |
| CH | 482 807 A | | 12/1969 | C09B/62/28 |
| DE | 19962228 | * | 12/1999 | |
| EP | 0 356 394 A2 | | 2/1990 | C09B/62/20 |
| FR | 1.392.152 A | | 6/1965 | |

OTHER PUBLICATIONS

Lehr, F., "Synthesis and Application of Reactive Dyes with Heterocyclic Reactive Systems," Jan. 19, 1990, pp. 239–263.

* cited by examiner

*Primary Examiner*—Yogendra N. Gupta
*Assistant Examiner*—Ann-Marie Koss
(74) *Attorney, Agent, or Firm*—Brent M. Peebles; Stephen T. Murphy; Tara M. Rosnell

(57) ABSTRACT

This invention relates to reactive dye compounds, and more especially to reactive dye compounds comprising a chromophore and a nitroen-containing heterocycle comprising at least one thio-substituent. The reactive dye compounds of the present are particularly suitable for dyeing hair.

10 Claims, No Drawings

REACTIVE DYE COMPOUNDS

This application is a continuation of PCT/US98/06561, filed Apr. 2, 1998.

TECHNICAL FIELD

This invention relates to reactive dye compounds, and more especially to reactive dye compounds comprising a chromophore and a nitrogen-containing heterocycle comprising at least one thio-substituent. The reactive dye compounds of the present are particularly suitable for dyeing hair.

BACKGROUND OF THE INVENTION

The desire to alter the color of human hair is not a facet of modern times. Since the days of the Roman Empire the color of human hair has been routinely altered to accommodate the changes of fashion and style. However the attainment of precise initial colors which are retained by the hair for a desirable period has remained a more elusive goal. The difficulties in the development of hair coloring compositions which can deliver precise long-lasting colors are in part due to the inherent structure of the hair itself and in part due to the necessary conditions of effective hair coloration processes.

In general, the condition and structure of human hair is not regular along the length of the hair shaft. Human hair is subject to various chemical and mechanical treatments such as combing, brushing, shampooing, heating, perming as well as exposure to the sun. As such, the hair at the ends of the hair shaft will generally exhibit greater signs of damage relative to the new growth close to the scalp. This damage can lead to inconsistent coloration when the hair is dyed due to irregular uptake of the hair coloring agents along the length of the hair shaft.

Once the hair has been colored there is a desire for the color to be resistant to fading, as occasioned by the actions of washing (also known as wash fastness), perspiration, hair spray and other exterior factors such as the action of the sun, and further that the color be retained in a consistent manner for a predictable period of time. Additionally damage to the hair that can lead to irregular dye uptake as discussed above, can lead to increased fading of the damaged portions of the hair and consequently, irregular levels of color fade over time. An additional difficulty commonly associated with the dyeing of human hair is the need for dye systems which avoid any adverse effect on the hair and skin of the user, such as brittle hair, or, irritation of the skin, or, staining (coloring) of the skin.

Thus, it would be desirable to develop a hair coloring composition which exhibits reduced fade, provides improved resistance to wash out during a regular cleansing regimen, can deliver substantially consistent hair color results throughout the hair, which has reduced irritant effect on the skin, which has reduced staining on the skin, which has reduced adverse effects on the hair of the user and also to develop a convenient and easy-to-use method for the delivery of such a hair coloring composition to the hair.

Over the years significant effort has been directed towards the elimination of many of the problems associated with the dyeing of human hair. Various approaches to hair dyeing have been developed, these include, oxidative dyes, direct action dyes, natural dyes, metallic dyes and reactive dyes.

GB-A-0,951,021 (Turner-Hall Corporation) relates to methods and compositions for dyeing keratinous fibres by attaching a dyestuff molecule to a particular site thereof through true covalent bonds. The method comprises reducing some of the disulfide linkages of the cystine in the fibers to sulfhydryl groups while breaking hydrogen bonds by applying to the fibers in alkaline aqueous solution a reducing agent for breaking disulfide linkages of keratinous fibres and a hydrogen bond breaker for keratinous fibres and bonding a water-soluble fibre reactive dye compound such as a dichlorotriazine dye to the sulfhydryl groups by applying an aqueous solution of the fibre reactive dye. Thioglycolic acid is disclosed as a reducing agent.

U.S. Pat. No. 3,415,606 discloses a method for dyeing human hair comprising the steps of treating said hair with an effective amount of mercaptan and then treating the hair with a dichlorotriazine fibre reactive dye.

"The Reaction Mechanism of Fibre Reactive Dyestuffs with Hair Keratin", Albert Shansky, American Perfumer and Cosmetics, November 1966, and "Dyeing of Human Hair with Fibre Reactive Dyestuffs", Albert Shansky, Cosmetics and Toiletries, November 1976, disclose a method of coloring hair comprising treating the hair for five minutes with a reducing-H bond breaking solution (containing thioglycolate, alkali, lithium bromide and urea) followed by rinsing the hair and then treating the hair with a dichlorotriazine fibre reactive dye.

Dyes and Pigments 14, 1990, pages 239–263, "Synthesis and Application of Reactive Dyes with Heterocyclic Reactive Systems" discloses fibre reactive dyes containing chlorotriazine heterocycles with thio substituents.

Reactive dye hair coloring agents can be used to deliver a variety of hair colors to the hair. However substantial improvement is needed in the areas of color saturation, color development, precise initial color consistency, improved wash fastness, improved hair condition and levels of hair damage.

Thus there is a need for reactive dye hair coloring compounds and compositions which effectively dye the hair but avoid or reduce damage to the hair, which can color the hair effectively and avoid or reduce irritation and/or staining to the skin of the user.

It has surprisingly been found that the reactive dye compounds of the present invention comprising a nitrogen-containing heterocycle selected from quinoxaline, pyridone or pyrimidone, substituted with at least one thio-derivative, provides improvements in colour saturation, colour development, colour consistence, wash fastness, hair condition, and reduction in hair damage and skin irritation.

In addition, conventional, reactive dye hair coloring compositions typically comprise at least two separately packaged components, which are generally, reducing agent and reactive dye hair coloring agents. These separately packaged components are admixed just prior to application to the hair. Such an admixing step can be messy and inconvenient to the user. Typically, such coloring compositions need to be used soon after admixing due to degradation of the resulting coloring composition. As such, excess admixed coloring composition is disposed of after application of the required amount to the hair. It has been found that the reactive dyes of the present invention can be incorporated in a singly packaged mixture with improved stability versus conventional reactive dye systems. The singly packaged coloring compositions of the present invention are suitable for use in a multi-application format (i.e. the consumer can use a single package for several color applications over a period of time). It has also been found that the reactive dye compounds and compositions herein are stable over time, and can be stored as such.

All percentages are by weight of the final compositions in the form intended to be used unless specified otherwise.

SUMMARY OF THE INVENTION

According to the present invention there is provided a reactive dye compound having the formula:

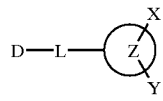

wherein
D is a chromophore,
X and Y are independently selected from SR', Cl, Br, or F, wherein R' is selected from: H, $C_1$–$C_4$ alkyl, $(CH_2)_n$COOH, $(CH_2)_n$CONH$_2$, $(CH_2)_n$SO$_3$H, $(CH_2)_n$COOM, $(CH_2)_n$PO$_3$H, $(CH_2)_n$OH, $(CH_2)_n$SSO$_3^-$, $(CH_2)_n$NR''$_2$, $(CH_2)_n$N$^+$R''$_3$, PhSSO$_3^-$, PhSO$_3$H, PhPO$_3$H, PhNR''$_2$, PhN$^+$R''$_3$, —CN, SO$_3^-$, $(CH_2)_2$CH(SH)R''$(CH_2)_3$COOH, —CH$_2$CHOHCH$_2$SH, and

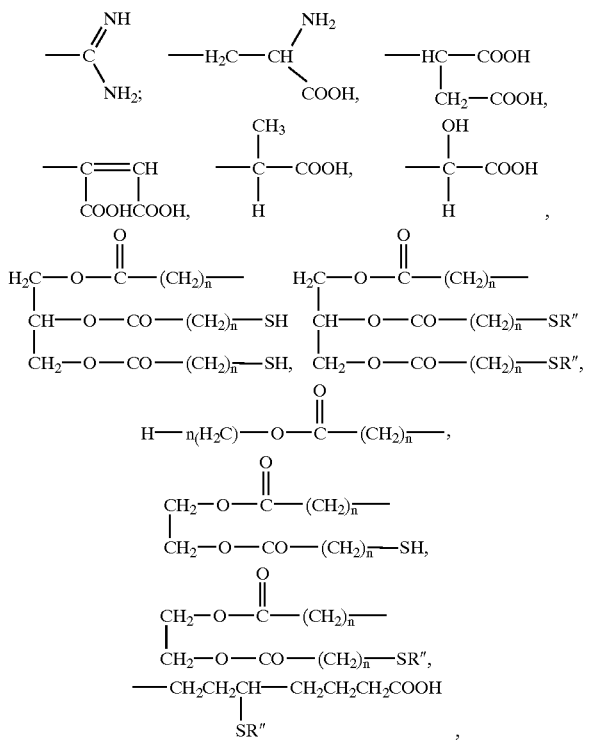

—CH$_2$CH$_2$NH$_2$.

"n is an integer in the range of 1 to 4 wherein within the same molecule n is not necessarily the same integer; and M is a cation of alkaline earth metal, alkali metal, NH$_4^+$ or N''$_3^+$.

L is a linking moiety;

Z is a nitrogen containing heterocycle selected from pyridone, quinoxaline or pyrimidone, R" is C1–C4 alkyl provided that at least one of X or Y is SR' and esters and salts thereof."

The reactive dye compounds of the present invention provide improved wash fastness of dye on hair and less colour fade over time.

DETAILED DESCRIPTION OF THE INVENTION

The reactive dye compounds herein comprise a nitrogen-containing heterocycle, a chromophore moiety, a linking group to link the nitrogen-containing heterocycle to the chromophore.

The reactive dye compounds herein have the formula (I):

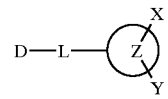

wherein
D is a chromophore;
X and Y are independently selected from SR', Cl, Br, or F, wherein R' is selected from: H, $C_1$–$C_4$ alkyl, $(CH_2)_n$COOH, $(CH_2)_n$CONH$_2$, $(CH_2)_n$SO$_3$H, $(CH_2)_n$COOM, $(CH_2)_n$PO$_3$H, $(CH_2)_n$OH, $(CH_2)_n$SSO$_3^-$, $(CH_2)_n$NR''$_2$, $(CH_2)_n$N$^+$R''$_3$, PhSSO$_3^-$, PhSO$_3$H, PhPO$_3$H, PhNR''$_2$, PhN$^+$R''$_3$, —CN, SO$_3^-$, $(CH_2)_2$CH(SH)R''$(CH_2)_3$COOH, —CH$_2$CHOHCH$_2$SH, and

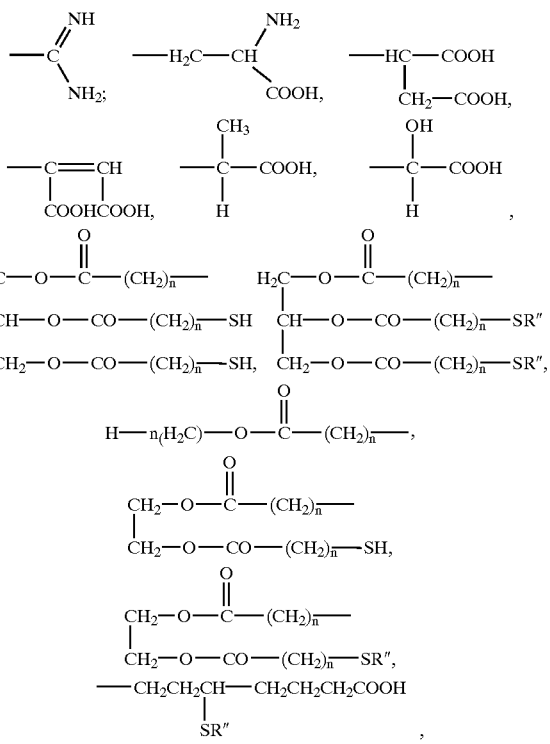

"n is an integer in the range of 1 to 4 wherein within the same molecule n is not necessarily the same integer; and M is a cation of alkaline earth metal, alkali metal, NH$_4^+$ or NR''$_3^+$.

L is a linking moiety;

Z is a nitrogen containing heterocycle selected from pyridone, quinoxaline or pyrimidone;

R" is C1–C4 alkyl provided that at least one of X or Y is SR' and esters and salts thereof."

Chromophore Moiety

Any chromophore moieties suitable for use for dying substrates can be used in the present invention. The term chromophore as used herein means any photoactive compound and includes any coloured or non-coloured light absorbing species, eg. fluorescent brighteners, UV absorbers, IR absorbing dyes.

Suitable chromophore moieties for use in the dye compounds herein include the radicals of monoazo, disazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophore moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water-soluble properties of the dye compound.

Most preferred chromophore D groups for use herein are polysulphonated azo chromophores such as those present in Levafix (RTM) dyes commercially available from Dystar.

Nitrogen Containing Heterocycle

The nitrogen containing heterocycle herein is selected from quinoxaline, pyridone and pyrimidone, preferably quinoxaline.

The nitrogen containing heterocycle has at least one thio substituent SR' wherein R' is selected from H, $C_1$–$C_4$ alkyl, $(CH_2)_n COOH$, $(CH_2)_n CONH_2$, $(CH_2)_n SO_3H$, $(CH_2)_n COOM$, $(CH_2)_n PO_3H$, $(CH_2)_n OH$, $(CH_2)_n SSO_3^-$, $(CH_2)_n NR''_2$, $(CH_2)_n N^+R''_3$, $PhSSO_3^-$, $PhSO_3H$, $PhPO_3H$, $PhNR''_2$, $PhN^+R''_3$, —CN, $SO_3^-$, $(CH_2)_2CH(SH)R''(CH_2)_3$ COOH, —$CH_2CHOHCH_2SH$, and

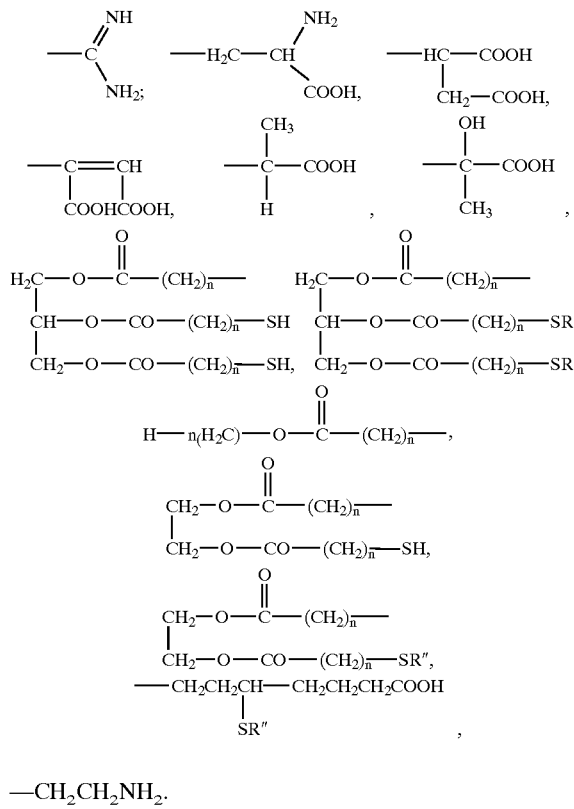

—$CH_2CH_2NH_2$.

n is an integer in the range of 1 to 4 wherein within the same molecule n is not necessarily the same integer; and M is a cation of alkaline earth metal, alkali metal, $NH_4^+$ or $NR''_3^+$.

Preferred R' groups for use herein are CH2COOH, CH2CH2OH and (COOH) CH2CH2(COOH), preferably CH2COOH.

The nitrogen-containing heterocycle may be substituted by two SR' groups or by one SR' group and one halogen group, preferably by two SR' groups.

Linking Moiety

The compounds herein further comprise a linking moiety to link each nitrogen-containing heterocycle to each chromophore moiety. Any linking moieties suitable for use in dyeing substrates can be used in the present invention. Preferably the linking moiety is selected from NR, NRC=O, C(O)NR, NRSO$_2$ and —SO$_2$NR wherein R is H or $C_1$–$C_4$ alkyl which can be substituted by halogen, preferably fluorine or chlorine, hydroxyl, cyano, $C_1$–$C_4$ alkoxy, $C_2$–$C_5$ alkoxycarbonyl, carboxyl, sulfamoyl, sulfo or sulfato. When the heterocycle is quinoxaline or phthalazine, a preferred linking moiety is NRC=O, where R is H or C1–C4 alkyl, more preferably where R is H or $CH_3$, especially H.

The present invention furthermore relates to processes for the preparation of dyes herein. In general, dyes having the formula (I) can be prepared by reacting suitable precursors of the dye of formula (I) with one another, at least one of which contains a group D-L-Z, wherein D, L and Z are as defined above, at least one of which contains an SR' group (wherein R' is as defined above).

For example, dye compounds of the invention having a formula (I) wherein Z is a quinoxaline heterocycle can be prepared by reacting a dichloroquinoxaline dye such as those commercially available from Dystar under the tradename Levofix E (RTM), with a suitable reactant containing an SR' group and then reacting the intermediate dye obtained with a suitable reactant containing a Q group.

The reactions of the starting dye compounds with the reactant containing an SR' group are generally carried out at a pH of from about 7 to about 10, and at a temperature of about 0–5 C. The reactions of the intermediate dye compounds with the reactant containing a Q group are generally carried out at a pH of from about 5 to about 6 and at a temperature of from about 50–85 C.

The dye compounds herein are particularly suitable for dyeing hair but are also suitable for dyeing and printing a wide variety of substrates, such as silk, leather, wool, polyesters, polyamide fibers and polyurethanes, and in particular cellulosic materials, such as the natural cellulose fibres, cotton, linen, hemp and the like, and also cellulose itself and regenerated cellulose, and hydroxyl-containing fibres contained in blend fabrics, for example blends of cotton with polyester or polyamide fibres. Thus in accordance with another aspect of the present invention there is provided a use of the compounds herein for dyeing hair and cotton, and the like.

The dye compounds herein can be incorporated into dye compositions together with suitable carrier materials which are selected depending on what type of substrate is being dyed. Such carrier materials will be well known to those skilled in the art.

The dye compounds herein are particularly suitable for dyeing hair and thus in accordance with another aspect of the present invention there is provided a hair dye composition comprising a compound having the formula (I) as described herein together with a suitable carrier.

Any carrier materials suitable for use in hair dye compositions can be used herein.

The compositions of the present invention comprise from about 0.01% to about 10%, preferably from about 0.1% to about 5%, especially from about 0.1% to about 3% by weight of one or more reactive dye compounds having the formula (I). The types and levels of dyes used in each composition will depend upon the desired hair shade.

A preferred ingredient in the hair dye compositions herein is a reducing agent. Any reducing agents suitable for use in hair dye compositions may be used herein. Some typical reducing agents for use herein are listed in GB-A-951,021 and GB-A-589,956, incorporated herein by reference. Examples of suitable reducing agents include thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols and hydroquinone. Particularly suitable for use herein are peglyated thiols.

Another preferred ingredient herein is a hydrogen bond breaker. Any hydrogen bond breaker suitable for use in a hair dye composition can be used herein. Suitable examples include lithium bromide, urea, resorcinol, catechol, dihydroxyacetone, formamide, potassium chloride and magnesium chloride. Particularly preferred for use herein is urea.

The coloring compositions of the present invention have a pH in the range of from about 7 to about 11, preferably from about 9 to about 10.5. In order to maintain such a pH the compositions may contain one or more optional buffering agents.

Examples of alkaline buffering agents are ammonium hydroxide, ethylamine, dipropylamine, itriethylamine and alkanediamines such as 1,3-diaminopropane, anhydrous alkaline alkanolamines such as, mono or di-ethanolamine, preferably those which are completely substituted on the amine group such as dimethylaminoethanol, polyalkylene polyamines such as diethylenetriamine or a heterocyclic amine such as morpholine as well as the hydroxides of alkali metals, such as sodium and potassium hydroxide, hydroxides of alkali earth metals, such as magnesium and calcium hydroxide, basic amino acids such as L-arginene, lysine, alanine, leucine, iso-leucine, oxylysine and histidine and alkanolamines such as dimethylaminoethanol and aminoalkylpropanediol and mixtures thereof. Also suitable for use herein are compounds that form $HCO_3^-$ by dissociation in water (hereinafter referred to as 'ion forming compounds'). Examples of suitable ion forming compounds are $Na_2CO_3$, $NaHCO_3$, $K_2CO_3$, $(NH4)_2CO_3$, $NH_4HCO_3$, $CaCO_3$ and $Ca(HCO_3)$ and mixtures thereof.

Preferred buffering agents for use herein are ammonium hydroxide, and sodium hydroxide.

The coloring compositions of the present invention may additionally include a thickener at a level of from about 0.05% to about 20%, preferably from about 0.1% to about 10%, more preferably from about 0.5% to about 5% by weight, Thickening agents suitable for use in the compositions herein are selected from oleic acid, cetyl alcohol, oleyl alcohol, sodium chloride, cetearyl alcohol, stearyl alcohol, synthetic thickeners such as Carbopol, Aculyn and Acrosyl and mixtures thereof Preferred thickeners for use herein are Aculyn 22 (RTM), steareth-20 methacrylate copolymer; Aculyn 44 (RTM), polyurethane resin and Acusol 830 (RTM), acrylates copolymer which are available from Rohm and Haas, Philadelphia, Pa., USA. Additional thickening agents suitable for use herein include sodium alginate or gum arabic, or cellulose derivatives, such as methyl cellulose or the sodium salt of carboxymethylcellulose or acrylic polymers.

Water is the preferred diluent for the compositions according to the present invention. However, the compositions according to the present invention may include one or more solvents as additional diluent materials. Generally, solvents suitable for use in the coloring compositions of the present invention are selected to be miscible with water and innocuous to the skin. Solvents suitable for use as additional diluents herein include $C_1-C_{20}$ mono- or polyhydric alcohols and their ethers, glycerine, with monohydric and dihydric alcohols and their ethers preferred. In these compounds, alcoholic residues containing 2 to 10 carbon atoms are preferred. Thus, a preferred group includes ethanol, isopropanol, n-propanol, butanol, propylene glycol, ethylene glycol monoethyl ether, and mixtures thereof Water is the preferred principal diluent in the compositions according to the present invention. Principal diluent, as defined herein, means, that the level of water present is higher than the total level of any other diluents.

The diluent is present at a level preferably of from about 5% to about 99.98%, preferably from about 15% to about 99.5%, more preferably at least from about 30% to about 99%, and especially from about 50% to about 98% by weight of the compositions herein.

The compositions of the present invention can additionally contain a surfactant system. Suitable surfactants for inclusion in the compositions of the invention generally have a lipophilic chain length of from about 8 to about 22 carbon atoms and can be selected from anionic, cationic, nonionic, amphoteric, zwitterionic surfactants and mixtures thereof.

(i) Anionic Surfactants

Anionic surfactants suitable for inclusion in the compositions of the invention include alkyl sulphates, ethoxylated alkyl sulphates, alkyl glyceryl ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl ethoxy carboxylates, alkyl phosphate esters, ethoxylated alkyl phosphate esters, alkyl sulphates, acyl sarcosinates and fatty acid/protein condensates, and mixtures thereof. Alkyl and/or acyl chain lengths for these surfactants are $C_{12}-C_{22}$, preferably $C_{12}-C_{18}$ more preferably $C_{12}-C_{14}$.

(ii) Nonionic Surfactants

The compositions of the invention can also comprise water-soluble nonionic surfactant(s). Surfactants of this class include $C_{12}-C_{14}$ fatty acid mono-and diethanolanides, sucrose polyester surfactants and polyhydroxy fatty acid amide surfactants having the general formula below.

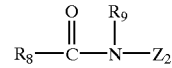

The preferred N-alkyl, N-alkoxy or N-aryloxy, polyhydroxy fatty acid amide surfactants according to the above formula are those in which $R_8$ is $C_5-C_{31}$ hydrocarbyl, preferably $C_6-C_{19}$ hydrocarbyl, including straight-chain and branched chain alkyl and alkenyl, or mixtures thereof and $R_9$ is typically hydrogen, $C_1-C_8$ alkyl or hydroxyalkyl, preferably methyl, or a group of formula —$R^1$—O—$R^2$ wherein $R^1$ is $C_2-C_8$ hydrocarbyl including straight-chain, branched-chain and cyclic (including aryl), and is preferably $C_2-C_4$ alkylene, $R^2$ is $C_1-C_8$ straight-chain, branched-chain and cyclic hydrocarbyl including aryl and oxyhydrocarbyl, and is preferably $C_1-C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars)

directly connected to the chain, or an alkoxylated derivative (preferably ethoxylated or propoxylated) thereof. $Z_2$ preferably will be derived from a reducing sugar in a reductive amination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of $-CH_2-(CHOH)_n-CH_2OH$, $-CH(CH_2OH)-(CHOH)_{n-1}-CH_2H$, $CH_2(CHOH)_2(CHOR')CHOH)-CH_2OH$, where n is an integer from 1 to 5, inclusive, and R' is H or a cyclic mono- or polysaccharide, and alkoxylated derivatives thereof As noted, most preferred are glycityls wherein n is 4, particularly $-CH_2-(CHOH)_4-CH_2OH$.

The most preferred polyhydroxy fatty acid amide has the formula $R_8(CO)N(CH_3)CH_2(CHOH)_4CH_2OH$ wherein $R_8$ is a C6–C19 straight chain alkyl or alkenyl group. In compounds of the above formula, $R_8-CO-N<$ can be, for example, cocoamide, stearamide, oleamide, lauramide, myristamide, capricamide, palmiamide, tallowamide, etc.

Suitable oil derived nonionic surfactants for use herein include water soluble vegetable and animal-derived emollients such as triglycerides with a polyethyleneglycol chain inserted; ethoxylated mono and di-glycerides, polyethoxylated lanolins and ethoxylated butter derivatives. One preferred class of oil-derived nonionic surfactants for use herein have the general formula below:

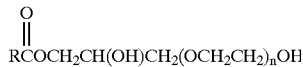

wherein n is from about 5 to about 200, preferably from about 20 to about 100, more preferably from about 30 to about 85, and wherein R comprises an aliphatic radical having on average from about 5 to 20 carbon atoms, preferably from about 7 to 18 carbon atoms.

Suitable ethoxylated oils and fats of this class include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Preferred for use herein are polyethyleneglycol based polyethoxylated $C_9-C_{15}$ fatty alcohol nonionic surfactants containing an average of from about 5 to about 50 ethyleneoxy moieties per mole of surfactant.

Suitable polyethylene glycol based polyethoxylated $C_9-C_{15}$ fatty alcohols suitable for use herein include $C_9-C_{11}$ Pareth-3, $C_9-C_{11}$ Pareth-4, $C_9-C_{11}$ Pareth-5, $C_9-C_{11}$ Pareth-6, $C_9-C_{11}$ Pareth-7, $C_9-C_{11}$ Pareth-8, $C_{11}-C_{15}$ Pareth-3, $C_{11}-C_{15}$ Pareth-4, $C_{11}-C_{15}$ Pareth-5, $C_{11}-C_{15}$ Pareth-6, $C_{11}-C_{15}$ Pareth-7, $C_{11}-C_{15}$ Pareth-8, $C_{11}-C_{15}$ Pareth-9, $C_{11}-C_{15}$ Pareth-10, $C_{11}-C_{15}$ Pareth-11, $C_{11}-C_{15}$ Pareth-12, $C_{11}-C_{15}$ Pareth-13 and $C_{11}-C_{15}$ Pareth-14. PEG 40 hydrogenated castor oil is commercially available under the tradename Cremophor (RTM) from BASF. PEG 7 glyceryl cocoate and PEG 20 glyceryl laurate are commercially available from Henkel under the tradenames Cetiol (RTM) HE and Lamacit (RTM) GML 20 respectively, $C_9-C_{11}$ Pareth-8 is commercially available from Shell Ltd under the tradename Dobanol (RTM) 91-8. Particulary preferred for use herein are polyethylene glycol ethers of ceteryl alcohol such as Ceteareth 25 which is available from BASF under the trade name Cremaphor A25.

Also suitable for use herein are nonionic surfactants derived from composite vegetable fats extracted from the fruit of the Shea Tree (Butyrospermum Karkii Kotschy) and derivatives thereof. Similarly, ethoxylated derivatives of Mango, Cocoa and Illipe butter may be used in compositions according to the invention. Although these are classified as ethoxylated nonionic surfactants it is understood that a certain proportion may remain as non-ethoxylated vegetable oil or fat, Other suitable oil-derived nonionic surfactants include ethoxylated derivatives of almond oil, peanut oil, rice bran oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil.

(iii) Amphoteric Surfactants

Amphoteric surfactants suitable for use in the compositions of the invention include:

(a) imidazolinium surfactants of formula (VII)

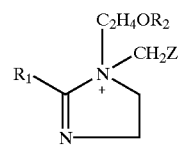

wherein $R_1$ is $C_7-C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (VIII)

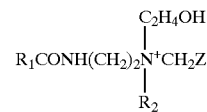

wherein $R_1$, $R_2$ and Z are as defined above;

(b) aminoalkanoates of formula (IX)

iminodialkanoates of formula (X)

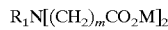

and iminopolyalkanoates of formula (XI)

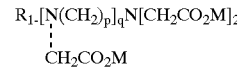

wherein n, m, p, and q are numbers from 1 to 4, and $R_1$ and M are independently selected from the groups specified above; and (c) mixtures thereof Suitable amphoteric surfactants of type (a) are marketed under the trade name Miranol and Empigen and are understood to comprise a complex mixture of species.

Traditionally, the Miranols have been described as having the general formula (VII), although the CTFA Cosmetic Ingredient Dictionary, 3rd Edition indicates the non-cyclic structure (VIII) while the 4th Edition indicates yet another structural isomer in which $R_2$ is O-linked rather than N-linked. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula XII and/or XIII in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials suitable for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special (Rh6ne-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals). Further examples of amphoteric surfactants suitable for use herein include Octoxynol-1 (RTM), polyoxethylene (1) octylphenyl ether; Nonoxynol-4 (RTM), polyoxyethylene (4) nonylphenyl ether and Nonoxynol-9, polyoxyethylene (9) nonylphenyl ether.

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Note also that the concentrations and weight ratios of the amphoteric surfactants are based herein on the uncomplexed forms of the surfactants, any anionic surfactant counterions being considered as part of the overall anionic surfactant component content.

Examples of preferred amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

(iv) Zwitterionic Surfactants

Water-soluble auxiliary zwitterionic surfactants suitable for inclusion in the compositions of the present invention include alkyl betaines of the formula $R_5R_6R_7N^+$ $(CH_2)_n$ $CO_2M$ and amido betaines of the formula (XII) below:

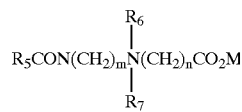

wherein $R_5$ is $C_{11}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, laurylamidopropyldimethylcarboxymethyl betaine and Tego betaine (RTM).

Water-soluble auxiliary sultaine surfactants suitable for inclusion in the compositions of the present invention include alkyl sultaines of the formula (XIII) below:

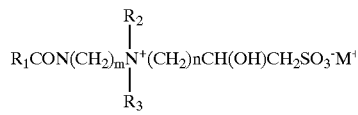

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Preferred for use herein is coco amido propylhydroxy sultaine.

Water-soluble auxiliary amine oxide surfactants suitable for inclusion in the compositions of the present invention include alkyl amine oxide $R_5R_6R_7NO$ and amido amine oxides of the formula (XIV) below:

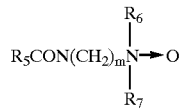

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

The hair coloring compositions of the present invention may, in addition to the essential reactive hair coloring agents, optionally include other dye materials. Optional other dyes suitable for use in the hair coloring compositions and processes according to the present invention include both semi-permanent, temporary and other dyes.

Suitable optional dyes for use herein include oxidative dyes. Any oxidative dye suitable for use in dyeing hair can be used in the compositions herein, for example those mentioned in WO98/27945, incorporated herein by reference in its entirety.

Non-oxidative dyes as defined herein include the so-called 'direct action dyes', metallic dyes, metal chelate dyes, fibre reactive dyes and other synthetic and natural dyes. Various types of non-oxidative dyes are detailed in: 'Chemical and Physical Behaviour of Human Hair' 3rd Ed. by Clarence Robbins (pp250–259); 'The Chemistry and Manufacture of Cosmetics'. Volume IV. 2nd Ed. Maison G. De Navarre at chapter 45 by G. S. Kass (pp841–920); 'cosmetics: Science and Technology' 2nd Ed., Vol. 11 Balsam Sagarin, Chapter 23 by F. E. Wall (pp 279–343); 'The Science of Hair Care' edited by C. Zviak, Chapter 7 (pp 235–261) and 'Hair Dyes', J. C. Johnson, Noyes Data Corp., Park Ridge, U.S.A. (1973), (pp 3–91 and 113–139).

Direct action dyes which do not require an oxidative effect in order to develop the color, are also designated hair tints and have long been known in the art. They are usually applied to the hair in a base matrix which includes surfactant material. Direct action dyes include nitro dyes such as the derivatives of nitroamino benzene or nitroaminophenol; disperse dyes such as nitroaryl amines, aminoanthraquinones or azo dyes; anthraquinone dyes, naphthoquinone dyes; basic dyes such as Acridine Orange C.I. 46005.

Nitrodyes are added to dyeing compositions to enhance colour of colorant and to add suitable aesthetic colour to the dye mixture prior to application.

Further examples of direct action dyes include the Arianor dyes basic brown 17, C.I.(color index)—no. 12,251; basic red 76, C.I.—12,245; basic brown 16, C.I.—12,250; basic yellow 57, C.I.—12,719 and basic blue 99, C.I.—56,059 and further direct action dyes such as acid yellow 1, C.I.—10, 316 (D&C yellow no.7); acid yellow 9, C.I.—13,015; basic violet C.I.—45,170; disperse yellow 3, C.I.—11,855; basic yellow 57, C.I.—12,719; disperse yellow 1, C.I.—10,345; basic violet 1, C.I.—42,535, basic violet 3, C.I.—42,555; greenish blue, C.I.—42090 (FD&C Blue no.1); yellowish red, C.I.—14700 (FD&C red no.4); yellow, C.I.19140 (FD&C yellow no5); yellowish orange, C.I.15985 (FD&C yellow no.6); bluish green, C.I.42053 (FD&C green no.3); yellowish red, C.I.16035 (FD&C red no.40); bluish green, C.I.61570 (D&C green no.3); orange, C.I.45370 (D&C orange no.5); red, C.I.15850 (D&C red no.6); bluish red, C.I.15850(D&C red no.7); slight bluish red, C.I.45380 (D&C red no.22); bluish red, C.I.45410(D&C red no.28); bluish red, C.I.73360(D&C red no.30); reddish purple, C.I.17200(D&C red no.33); dirty blue red, C.I.15880(D&C red no.34); bright yellow red, C.I.12085(D&C red no.36); bright orange, C.I.15510(D&C orange no.4); greenish yellow, C.I.47005(D&C yellow no.10); bluish green, C.I.59040(D&C green no.8); bluish violet, C.I.60730(Ext. D&C violet no.2); greenish yellow, C.I.10316(Ext. D&C yellow no.7);

Other fibre reactive dyes include the Procion (RTM), Drimarene (RTM), Cibacron (RTM), Levafix (RTM) and Remazol (RTM) dyes available from ICI, Sandoz, Ciba-Geigy, Bayer and Hoechst respectively.

Natural dyes and vegetable dyes as defined herein include henna (*Lawsonia alba*), camomile (*Matricaria chamomila* or *Anthenils nobilis*), indigo, logwood and walnut hull extract.

Temporary hair dyes, or hair coloring rinses, are generally comprised of dye molecules which are too large to diffuse into the hair shaft and which act on the exterior of the hair. They are usually applied via a leave-in procedure in which the dye solution is allowed to dry on the hair surface. As such these dyes are typically less resistant to the effects of washing and cleaning the hair with surface active agents and are washed off of the hair with relative ease. Any temporary hair dye may suitably be used in the compositions of the invention and examples of preferred temporary hair dyes are illustrated below.

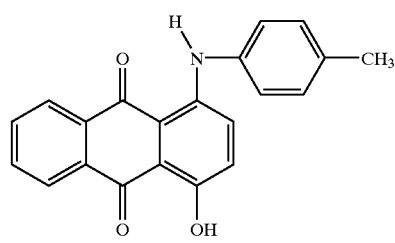
Violet

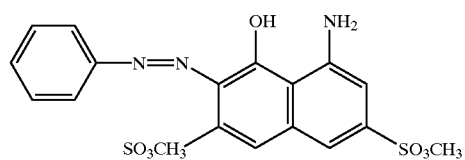
Red

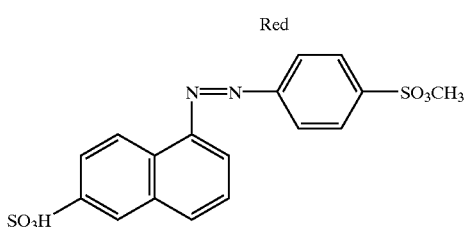
Yellow

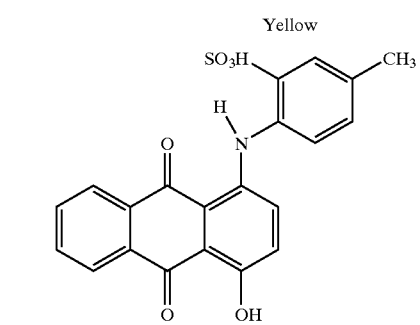
Blue-Violet

Semi-permanent hair dyes are dyes which are generally smaller in size and effect to temporary hair rinses but are generally larger than permanent (oxidative) dyes. Typically, semi-pennanent dyes act in a similar manner to oxidative dyes in that they have the potential to diffuse into the hair shaft. However, semi-permanent dyes are generally smaller in size than the aforementioned conjugated oxidative dye molecules and as such are pre-disposed to gradual diffusion out of the hair again. Simple hair washing and cleaning action will encourage this process and in general semi-permanent dyes are largely washed out of the hair after about 5 to 8 washes. Any semi-permanent dye system may be suitably used in the compositions of the present invention. Suitable semi-permanent dyes for use in the compositions of the present invention are HC Blue 2, HC Yellow 4, HC Red 3, Disperse Violet 4, Disperse Black 9, HC Blue 7, HC Yellow 2, Disperse Blue 3, Disperse violet 1 and mixtures thereof Examples of semi-permanent dyes are illustrated below:

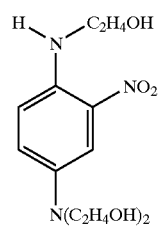
Blue

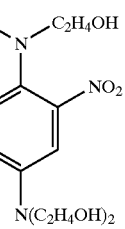
Blue

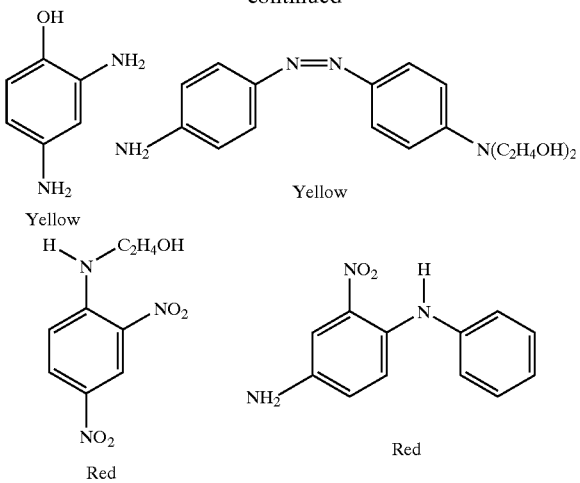

Typical semi-permanent dye systems incorporate mixtures of both large and small color molecules. As the size of the hair is not uniform from root to tip the small molecules will diffuse both at the root and tip, but will not be retained within the tip, while the larger molecules will be generally only be able to diffuse into the ends of the hair. This combination of dye molecule size is used to help give consistent color results from the root to the tip of the hair both during the initial dyeing process and during subsequent washing.

A number of additional optional materials can be added to the coloring compositions herein described each at a level of from about 0.001% to about 5%, preferably from about 0.01% to about 3%, more preferably from about 0.05% to about 2% by weight of composition. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol, benzoic acid, sodium benzoate and 2-phenoxyethanol; antioxidants such as sodium sulphite, hydroquinone, sodium bisulphite, sodium metabisulphite, sodium dithionite, erythrobic acid and other mercaptans; dye removers such as oxalic acid, sulphated castor oil, salicylic acid and sodium thiosulphate; $H_2O_2$ stabilisers such as tin compounds such as sodium stannate, stannic hydroxide and stannous octoate, acetanilide, phenacetin colloidal silica such as magnesium silicate, oxyquinoline sulphate, sodium phosphate, and tetrasodium pyrophosphate; and p-hydroxybenzoates; moisturising agents such as hyaluronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663 as well as methyl cellulose, starch, higher fatty alcohols, paraffin oils, fatty acids and the like; solvents; anti-bacterial agents such as Oxeco (phenoxy isopropanol); low temperature phase modifiers such as ammonium ion sources (e.g. $NH_4Cl$); viscosity control agents such as magnesium sulfate and other electrolytes; quaternary amine compounds such as distearyl-, dilauryl-, di-hydrogenated beef tallow-, dimethyl ammonium chloride, dicetyldiethyl ammoniumethylsulphate, ditallowdimethyl ammonium methylsulphate, disoya dimethyl ammonium chloride and dicoco dimethyl ammonium chloride; hair conditioning agents such as silicones, higher alcohols, cationic polymers and the like, enzyme stabilisers such as water soluble sources of calcium or borate species; colouring agents; $TiO_2$ and $TiO_2$-coated mica; perfumes and perfume solubilizers; and zeolites such as Valfour BV400 and derivatives thereof and $Ca^{2+}/Mg^{2+}$ sequestrants such as polycarboxylates, amino polycarboxylates, polyphosphonates, amino polyphosphonates etc. and water softening agents such as sodium citrate.

The present invention is represented by the following non-limiting examples. In the examples, all concentrations are on a 100% active basis and all percentages are by weight unless otherwise stated and the abbreviations have the following designations.

EXAMPLE 1

Synthesis of Chlorothioglycolato Quinoxaline Dye

The chlorothioglycolato quinoxaline dye is prepared using the synthesis route as illustrated in Diagram 1.

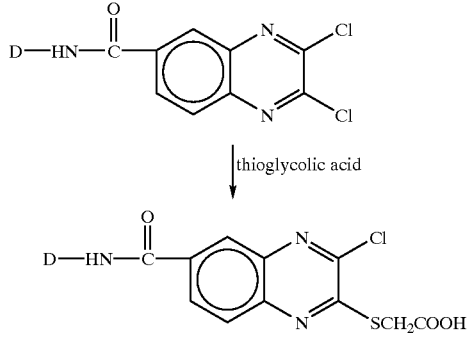

Diagram I

In the reaction scheme D is a chromophore and varies depending on which starting dye is used. In the present example, Levafix Goldgelb E-G commercially available from DyStar is used a starting material but this can be replaced by any suitable quinoxaline dye such as Levafix Brilliant Blue E-B, Levafix Brilliant Red E-RN and Levafix Brown E-2R.

Synthesis of Monothioglycolatoguinoxaline Dye 0.1 moles of pure Levafix Goldgelb E-G dye and 150 ml distilled water are introduced into a flask. 0.1 moles of mercaptoacetic acid is then added dropwise to the reaction mixture with stirring. The total addition time is 1 hour. The pH of the reaction system is maintained at pH 9 and the temperature of the reaction system 30–35° C. throughout the addition of mercaptoacetic acid.

The reaction is then allowed to proceed at 30–35° C. and pH 9 (which is corrected using sodium carbonate and HCl) for 4–5 hours. The end-of-reaction point for this part of the synthesis is indicated by the pH of the reaction system remaining constant for more than 5 minutes. At this point, thioglycolato quinoxaline dye is obtained. Using 6N HCl, the pH of the system is then reduced to below pH2 to terminate the reaction. KCl (≡35% of the total solution) is then added to the reaction mixture in order to precipitate the dye. Filtration using Whatman filter paper follows. The precipitate is then washed with acetone for 4–5 times (≡50 ml of acetone used each time to obtain the dye product.

EXAMPLE 2

The compounds according to Example 1 can be included in a hair coloring composition.

| Auburn Dye | |
|---|---|
| Ingredients | % |
| Urea | 10.00 |
| Cocamidopropyl Betaine | 0.80 |
| Red Dye from Eg 1 | 0.23 |
| Yellow Dye from Eg 1 | 0.42 |
| Blue Dye from Eg. 1 | 0.35 |
| Thioglycolic Acid 80% | 9.26 |
| Triethanolamine 99% | 50.74 |
| Ammonium Hydroxide 29% | 9.00 |
| Water | to 100 |

What is claimed is:

1. Reactive dye compound having the formula:

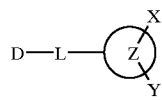

wherein

D is a chromophore;

X and Y are SR', wherein R' is selected from the group consisting of: H, $C_1$–$C_4$ alkyl, $(CH_2)_nCOOH$, $(CH_2)_nCONH_2$, $(CH_2)_nSO_3H$, $(CH_2)_nCOOM$, $(CH_2)_nPO_3H$, $(CH_2)_nOH$, $(CH_2)_nSSO_3^-$, $(CH_2)_nNR''_2$, $(CH_2)_nN^+R''_3$, $PhSSO_3^-$, $PhSO_3H$, $PhPO_3H$, $PhNR''_2$, $PhN^+R''_3$, —CN, $SO_3^-$, $(CH_2)_2CH(SH)R''(CH_2)_3COOH$, —$CH_2CHOHCH_2SH$, and

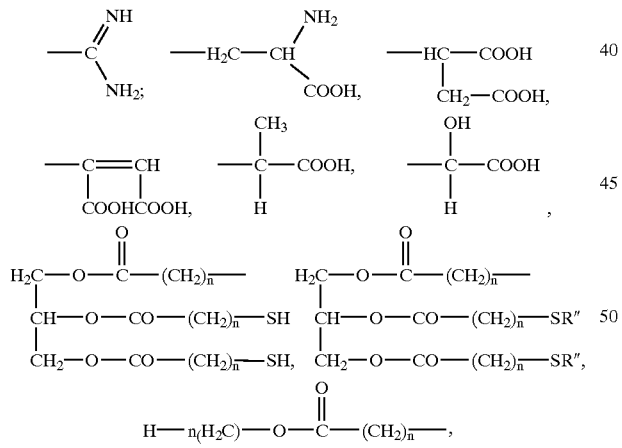

—$CH_2CH_2NH_2$;

n is an integer in the range of 1 to 4 wherein within the same molecule n is not necessarily the same integer; and M is a cation of alkaline earth metal, alkali metal, $NH_4^+$ or $NR''_3^+$;

L is a linking moiety;

Z is a nitrogen containing heterocycle selected from the group consisting of pyridone, quinoxaline and pyrimidone;

R" is C1–C4 alkyl and esters and salts thereof.

2. A reactive dye compound according claim 1 or 2 wherein Z is quinoxaline.

3. A reactive dye compound according to claim 1 wherein L is selected from the group consisting of NR, NRC=O, C(O)NR, $NRSO_2$ and —$SO_2NR$ wherein R is H or $C_1$–$C_4$ alkyl which can be substituted by halogen, hydroxyl, cyano, $C_1$–$C_4$ alkoxy, $C_2$–$C_5$ alkoxycarbonyl, carboxyl, sulfamoyl, sulfo or sulfato.

4. A reactive dye compound according to claim 3 wherein L is NR.

5. A reactive dye compound according to claim 4 wherein R is selected from the group consisting of C1–C4 alkyl and H.

6. A reactive dye compound according to claim 1 wherein R' is $CH_2COOH$.

7. A dye composition suitable for dyeing hair comprising a reactive dye compound according to any of claim 1 and a carrier.

8. A method for dyeing hair comprising the steps of:
   a) applying the reactive dye compound of claim 1 to hair; and
   b) removing said reactive dye compound from the hair.

9. A method for dyeing textiles comprising the steps of:
   a) applying the reactive dye compound of claim 1 to textiles; and
   b) removing said reactive dye compound from the textiles.

10. A reactive dye compound according to claim 4 wherein R is selected form H.

* * * * *

UNITED STATES PATENT AND TRADEMARK OFFICE
CERTIFICATE OF CORRECTION

PATENT NO.     : 6,447,554 B1
DATED          : September 10, 2002
INVENTOR(S)    : Earl David Brock et al.

It is certified that error appears in the above-identified patent and that said Letters Patent is hereby corrected as shown below:

Column 4,
Line 54, insert -- -$CH_2CH_2NH_2$ --.

Column 7,
Line 29, "itriethylamine" should read -- triethylamine --.

Column 8,
Line 45, "diethanolanides" should read -- diethanolamides --.

Signed and Sealed this

Seventh Day of January, 2003

JAMES E. ROGAN
*Director of the United States Patent and Trademark Office*